United States Patent [19]

Austin et al.

[11] Patent Number: 5,315,009

[45] Date of Patent: May 24, 1994

[54] PREPARATION OF ISOTHIAZOLINONES FROM DISULPHIDES AND DISULPHIDES FROM ISOTHIAZOLINONES

[75] Inventors: Peter W. Austin, Bury, England; Neville Tyreman, Llanfairfechan, Wales

[73] Assignee: Imperial Chemical Industries PLC, London, England

[21] Appl. No.: 31,712

[22] Filed: Mar. 15, 1993

Related U.S. Application Data

[62] Division of Ser. No. 763,276, Sep. 20, 1991, Pat. No. 5,224,980.

[30] Foreign Application Priority Data

Sep. 26, 1990 [GB] United Kingdom ................. 9020933

[51] Int. Cl.$^5$ .................. C07D 275/06; C07C 323/41
[52] U.S. Cl. ..................................... 548/209; 564/154
[58] Field of Search ......................... 548/209; 564/154

[56] References Cited

U.S. PATENT DOCUMENTS

| | | |
|---|---|---|
| 2,470,945 | 5/1946 | Paul .................................... 260/30.8 |
| 3,012,039 | 12/1961 | Morley ................................. 564/154 |
| 3,300,378 | 1/1967 | Fischer et al. ........................ 167/65 |
| 3,761,488 | 9/1973 | Lewis et al. .......................... 260/302 |
| 3,914,301 | 10/1975 | Miller et al. ....................... 260/561 S |
| 4,165,318 | 8/1979 | Greenfield et al. ............. 360/302 A |
| 4,190,663 | 2/1980 | Börhagen et al. .................. 424/267 |
| 4,705,805 | 11/1987 | Yamada et al. ..................... 514/548 |
| 4,727,188 | 2/1988 | Jaedicke .............................. 564/154 |
| 4,751,311 | 6/1988 | Backhouse .......................... 548/209 |
| 4,851,541 | 7/1989 | Maignan et al. .................... 548/209 |

FOREIGN PATENT DOCUMENTS

| | | |
|---|---|---|
| 0001193 | 3/1979 | European Pat. Off. . |
| 0187349 | 7/1986 | European Pat. Off. . |
| 0342105 | 11/1989 | European Pat. Off. . |
| 0410726 | 1/1991 | European Pat. Off. . |
| 295486 | 5/1971 | Fed. Rep. of Germany . |
| 2821639 | 3/1979 | Fed. Rep. of Germany . |
| 198418 | 11/1983 | Japan . |
| 1532984 | 11/1978 | United Kingdom . |
| 2087388 | 5/1982 | United Kingdom . |
| 2176187 | 12/1986 | United Kingdom . |

Primary Examiner—Richard L. Raymond
Attorney, Agent, or Firm—Cushman, Darby & Cushman

[57] ABSTRACT

A compound of the formula

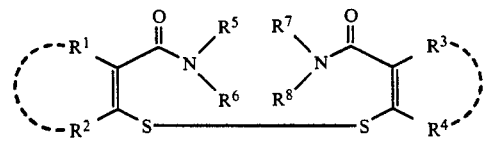

in which $R^1$ and $R^2$ taken together, and $R^3$ and $R^4$ taken together, independently represent a polymethylene chain leaving 3 or 4 carbon atoms, or a polymethylene chain having 3 or 4 carbon atoms substituted by at least one lower alkyl radical having from 1 to 4 carbon atoms and $R^5$ to $R^8$ are independently hydrogen, hydrocarbyl or substituted hydrocarbyl. Typically $R^1$ and $R^2$ and also $R^3$ and $R^4$ complete a trimethylene ring, $R^5$ and $R^7$ are each hydrogen and $R^6$ and $R^8$ are alkyl such as methyl. The compounds have microbiological activity.

8 Claims, No Drawings

PREPARATION OF ISOTHIAZOLINONES FROM DISULPHIDES AND DISULPHIDES FROM ISOTHIAZOLINONES

This is a division of application Ser. No. 07/763,276, filed Sep. 20, 1991 now U.S. Pat. No. 5,224,980.

The present invention relates to compounds which are useful as industrial biocides, and to the preparation and use of such compounds.

Industrial biocides are useful to prevent industrial spoilage, in particular that caused by bacteria and fungi. Industrial biocides find application in the preservation of paints, latices, adhesives, leather, wood, metal working fluids and cooling water.

One class of compound which can be used as an industrial biocide is based on the isothiazolinone structure. There are many disclosures of isothiazolinone derivatives which are stated to have useful biocidal properties. U.S. Pat. No. 3,761,488 discloses isothiazolinone derivatives in which alkyl, alkenyl, alkynyl, cycloalkyl, aralkyl or aryl groups, which may optionally be substituted, are attached to the nitrogen atom and the 4 and 5 positions are unsubstituted or are substituted with halogen or lower alkyl groups. U.S. Pat. No. 4,165,318 discloses a solution of an isothiazolin-3-one in a polar organic solvent, wherein the solution also contains a stabilising amount of formaldehyde. British Patent Specification 2087388 discloses 4,5-polymethylene-4-isothiazolin-3-ones in which the polymethylene chain has three or four carbon atoms.

A further class of compounds which have found use as industrial biocides are the disulphides such as 2,2'-bis(methylaminocarbonyl)diphenyldisulphide whose use is described and claimed in British Patent Specification 1532984.

Both these classes of compounds have become commercially important as industrial biocides.

We have now discovered a new class of compounds which possess surprisingly useful antimicrobial and especially anti-bacterial properties and which are effective as industrial biocides.

According to the present invention, there is provided a compound of the general formula I

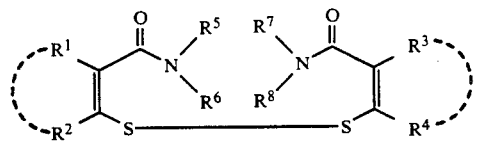

wherein:

$R^1$ and $R^2$ taken together, and $R^3$ and $R^4$ taken together, independently represent a polymethylene chain having 3 or 4 carbon atoms or a polymethylene chain having 3 or 4 carbon atoms substituted by at least one lower alkyl radical having from 1 to 4 carbon atoms; and $R^5$ to $R^8$ are each independently hydrogen, hydrocarbyl or substituted hydrocarbyl or $R^5$ and $R^6$ taken together with the nitrogen atom form a ring and/or $R^7$ and $R^8$ taken together with the nitrogen atom, form a ring.

When $R^1$ and $R^2$ form a polymethylene chain substituted by lower alkyl, there may be present up to eight lower alkyl radicals. It is preferred, however, that $R^1$ and $R^2$ contain no alkyl substituents.

In one particular embodiment of the invention where $R^1$ and $R^2$ taken together, and $R^3$ and $R^4$ taken together form a polymethylene chain, the compound is one of general formula II

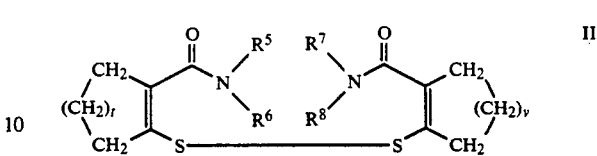

wherein
$R^5$ to $R^8$ are as previously defined; and
t and v are independently 1 or 2.

Preferably t and v are the same, and are especially both 1.

When $R^5$ to $R^8$ is hydrocarbyl or substituted hydrocarbyl, each of $R^5$, $R^6$, $R^7$ and $R^8$ may contain up to 20 carbon atoms, and especially up to 12 carbon atoms. When $R^5$ to $R^8$ is hydrocarbyl, it may be alkyl, aryl, cycloalkyl, alkaryl or alkenyl and when $R^5$ to $R^8$ is substituted hydrocarbyl, it is a hydrocarbyl moiety such as one of those mentioned hereinbefore which additionally contains or carries at least one hetero-atom selected from oxygen, nitrogen, sulphur and halogen, for example, fluorine chlorine and bromine.

When $R^5$ and $R^6$ together with the nitrogen atom, and/or $R^7$ and $R^8$ together with the nitrogen atom form a ring, the ring may contain further heteroatoms such as oxygen, sulphur and nitrogen. It is preferably a 5 or 6 membered ring such as a morpholino, piperidino or piperazino ring.

In a preferred embodiment of the compound of general formula I, $R^5$ is the same as $R^7$ and $R^6$ is the same as $R^8$.

It is generally preferred that $R^5$ to $R^8$ are hydrogen or hydrocarbyl especially alkyl, which may be linear or branched. Particularly useful compounds are those compounds of general formula II where t and v are both 1, and $R^5$ to $R^8$ are all hydrogen, and also those where $R^5$ and $R^7$ are both hydrogen and $R^6$ and $R^8$ are $C_1$-$C_{12}$ alkyl, especially $C_1$-$C_6$ alkyl, such as methyl. Specific examples are
bis-(2-aminocarbonylcyclopent-1-enyl)disulphide
bis-(2-methylaminocarbonylcyclopent-1-enyl)disulphide,
bis(2-butylaminocarbonylcyclopent-1-enyl)disulphide,
bis(2-hexylaminocarbonylcyclopent-1-enyl)disulphide and
bis(2-octylaminocarbonylcyclopent-1-enyl)disulphide.

The compounds of general formula I may be prepared by any convenient method, for example, by the controlled oxidation of a thiol-amide precursor of general formula IIIa and/or IIIb.

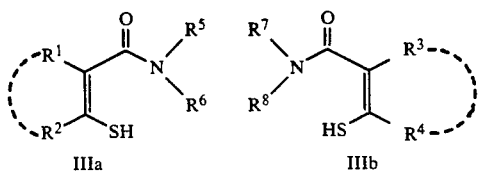

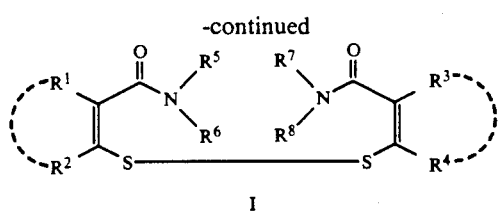

I

The conversion of the thiol-amides to the disulphide is preferably carried out under anhydrous conditions by suspending or preferably dissolving the thiol-amide in a suitable non-aqueous liquid medium. The liquid medium is chosen to suit the particular thiol-amide and the oxidising agent in question and is typically selected from alcohols such as methanol or ethanol, aromatic solvents such as toluene, aliphatic solvents such as hexane, and especially the chloro-aliphatic hydrocarbons such as methylene chloride, chloroform or tetrachloroethylene. Mixtures of solvents may also be used. However, under certain circumstances the liquid medium may be water provided the thiol-amide is sufficiently soluble in water and, more importantly the oxidising agent is compatible with water.

The oxidising agent may be selected from peroxy compounds such as hydrogen peroxide, alkali metal peroxides, organic peroxy compounds such as peracetic acid, halides such as chlorine, and bromine, and especially the oxyhalides of sulphur such as sulphuryl chloride. The oxidising agent may be supported on an inert carrier, for example, sodium metaperiodate on alumina. With most of the foregoing oxidising agents, the reaction should be carried out under substantially anhydrous conditions, preferably in one or more of the above-mentioned organic solvents.

The reaction of the thiol-amide occurs readily and is normally carried out at temperatures below 60° C. and typically below 30° C., for example between 0° and 10° C.

The choice of reaction conditions in terms of temperature, oxidising agent, solvent and concentration of reactants is important in the preparation of the disulphides of general formula I particularly the compounds in which $R^5$ and $R^7$ are hydrogen. If the oxidising agent is too strong or the conditions are too forcing or the ratio of oxidising agent to thiol-amide is too high, the reaction may proceed too far to give the analogous cyclic 4,5-polymethylene-4-isothiazolin-3-one or its further oxidation products.

We have now found that the thiol-amides of general formula IIIa and/or IIIb may be efficiently converted to the disulphide of general formula I by reacting the thiol-amide in a chloro-aliphatic hydrocarbon solvent at low temperature with approximately 0.5 moles sulphuryl chloride per mole of thiol.

Thus, according to a further feature of the invention there is provided a process for producing the disulphide of general formula I by reacting the thiol-amides of general formula IIIa and/or IIIb in a chloro-aliphatic hydrocarbon solvent such as methylene chloride with less than 1 mole of an oxyhalide of sulphur such as sulphuryl chloride and at a temperature of not greater than 60° C. Preferably, the reaction is carried out below 30° C., for example between 0° and 10° C. Ideally the proportion of the oxyhalide of sulphur is below 0.7 moles per mole of thiol-amide, especially below 0.5 moles/mole, for example between 0.3 and 0.5 moles/mole thiol-amide.

The conversion of the thiol-amide to disulphide may be monitored in conventional manner, such as by high performance liquid chromatography (HPLC) and the reaction stopped at the appropriate time to optimise the yield of the disulphide.

The disulphide of general formula I may be isolated and recovered by conventional means, such as evaporation of the solvent, extraction into water or by filtration and drying.

As mentioned hereinbefore the thiol-amide may be oxidised to the disulphide of general formula I or through to the analogous 4,5-polymethylene-4-isothiazolin-3-one depending on the nature of the oxidising agent used and the stoichiometric ratio of oxidising agent to thiol-amide. The disulphide of general formula I itself may, therefore, be converted to the isothiazolin-3-one. Consequently, the disulphides of general formula I wherein $R^5$ and $R^7$ are both hydrogen and $R^1$ to $R^4$ and $R^6$ and $R^8$ are as hereinbefore defined, are themselves valuable intermediates for the preparation of 4,5-polymethylene-4-isothiazolin-3-ones. The conversion of these disulphides to the cyclic isothiazolin-3-one is less dependant on the nature and the relative amount of the oxidising agent and disulphide, although if the conditions are too forcing oxidation beyond the isothiazolin-3-one can occur. The disulphides of general formula I exhibit relatively low solubility in water and organic solvents and the yield of the isothiazolin-3-one is, therefore, low. However, it has now been found that the disulphides of general formula I may be converted to the isothiazolin-3-one in high yield by carrying out the reaction in a mixture of a suitable organic solvent and a strong organic acid which is miscible with the organic solvent. The organic solvent is preferably inert and is preferably selected from chloro-aliphatic hydrocarbon solvents such as methylene chloride, and the strong organic acid is preferably formic acid.

The reaction occurs readily and is preferably carried out at temperature not above 60° C., more preferably below 30° C., and especially from 0° to 10° C.

The oxidising agent can be selected from any mentioned hereinbefore, especially the oxychlorides of sulphur, such as sulphuryl chloride.

In contrast to the oxidation of the thiol-amides to the disulphides of the general formula I, the oxidation of the disulphides to the cyclic 4,5-polymethylene-4-isothiazolin-3-ones generally requires more forcing conditions and is typically carried out with molar proportions of the oxidising agent in excess of 0.5 mole of oxidising agent/mole of disulphide. Although proportions of oxidising agent which are in excess of 10 moles/mole of disulphide may be used, we have found that there is no advantage and high concentrations of oxidising agent, high temperatures and long reaction times can result in unacceptable oxidation by-products of the isothiazolin-3-one. Thus, it is preferred to maintain the proportion of the oxidising agent, such as sulphuryl chloride in excess of 0.5 mole oxidising agent/mole of disulphide but below 10 moles of oxidising agent/mole of disulphide. Generally, we have found that high yields of the isothiazolin-3-one from the disulphide can be obtained with from 1 to 5 moles oxidising agent/mole of disulphide and especially with from 1 to 2 moles of oxidising agent/mole of disulphide more especially from 1 to 1.2 moles of oxidising agent.

Thus, as a still further embodiment of the present invention there is provided a process for making a 4,5-polymethylene-4-isothiazolin-3-one by the oxidation of a compound of general formula I, wherein $R^5$ and $R^7$ are both hydrogen and $R^1$ to $R^4$ and $R^6$ and $R^8$ are as hereinbefore defined. The product will be a mixture of two 4,5-polymethylene-4-isothiolin-3-ones where $R^1R^2$ and $R^3R^4$ are different and $R^6$ and $R^8$ are different.

It is generally preferred when preparing such isothiazolinones from the disulphides of general formula I that $R^1$ and $R^2$ are the same as $R^3$ and $R^4$ and $R^6$ and $R^8$ are the same so that a single product is produced.

Thus, there is provided a process for making a 4,5-polymethylene4-isothiazolin-3-one of general formula IV

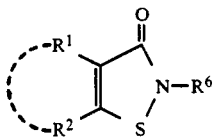

by oxidising a disulphide of general formula V

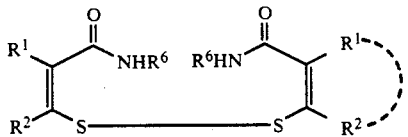

wherein $R^1$, $R^2$ and $R^6$ are as hereinbefore defined.

The oxidation may be carried out in an inert organic solvent but, because of the low solubility of the disulphides of general formula V, it is generally preferred to use a mixture of an inert organic solvent and a strong organic acid. The strong organic acid is preferably formic acid, and the inert organic solvent is preferably a chloro-aliphatic hydrocarbon, such as methylene chloride.

The oxidising agent is preferably an oxyhalide of sulphur, such as sulphuryl chloride. The proportion of oxidising agent is generally at least 0.5 moles of oxidising agent/mole of disulphide and less than 10 moles of oxidising agent/mole of disulphide. It is preferred that the amount of oxidising agent is from 1 mole to 5 moles of oxidising agent/mole of disulphide, especially from 1 mole to 2 moles of oxidising agent/mole of disulphide.

The reaction temperature is preferably not greater than 60° C., more preferably below 30° C., and especially from 0° to 10° C.

It will be appreciated that the isothiazolin-3-ones of general formula IV may be made directly from the disulphides of general formula V. Isothiazolin-3-ones of general formula IV wherein $R^6$ is hydrocarbyl or substituted hydrocarbyl may be made from the disulphides of general formula V wherein $R^6$ is hydrogen by oxidation to the isothiazolin-3-one of general formula IV wherein $R^6$ is hydrogen and reacting this with a suitable reagent comprising a hydrocarbyl or substituted hydrocarbyl radical, $R^6$. Suitable reagents are those described in British Patent Application 2087388.

The isothiazolin-3-ones can be isolated in a number of ways known to the art, such as filtration, or they may be recovered from solution by evaporating the solvent. For convenience, the isothiazolin-3-one may also be formulated for industrial usage without isolation from the organic phase, or it may be extracted into an aqueous phase and then formulated as an aqueous formulation without isolation.

It will be appreciated that, since the disulphide of general formula V may be oxidised to form the cyclic polymethylene isothiazolin-3-one of general formula IV, the isothiazolin-3-one may itself be reduced to form the disulphide.

Thus, as a still further embodiment of the present invention there is provided a process for preparing the disulphides of general formula V by reducing the 4,5-polymethylene-4-isothiazolin-3-one of general formula IV.

The reaction occurs readily, and is preferably carried out at temperatures not greater than 60° C., and preferably below 30° C., and especially from 0° to 20° C.

The reaction is preferably carried out in a polar solvent such as water, an alkanol such as methanol or ethanol, or in aqueous alkanol solutions.

Typical reducing agents are the alkali metal salts of bisulphite and hydrosulphite anions, especially the sodium salts.

Relatively high proportions of the reducing agents may be used, such as 10 moles of reducing agent per mole of isothiazolin-3-one. However, we have found that the reaction proceeds well with from 1 mole to 2 moles of reducing agent per mole of isothiazolin-3-one.

The reaction is typically carried out in solution in water or methanol by stirring together the isothiazolin-3-one and reducing agent. Under such conditions, the disulphide normally separates and may be recovered by filtration.

In many instances, it is more convenient on the laboratory scale to deposit the disulphide on a silica support and effect a purification and isolation by "flash chromatography". The disulphide in this case is selectively eluted from the silica in a suitable solvent or mixture of solvents of increasing polarity.

Certain of the thiol-amides of general formula IIIa or IIIb wherein $R^1$, $R^2$, $R^3$ and $R^4$ are as hereinbefore defined, and where $R^5$ and $R^7$ are hydrogen and $R^6$ and $R^8$ are hydrogen, hydrocarbyl or substituted hydrocarbyl have been disclosed in British Patent Application 2087388 which also discloses the preparation of such thiol-amides by the action of hydrogen sulphide on the 2-monosubstituted aminocarbonylcycloalken-1-one.

We have found that compounds of formula IIIa or IIIb may be readily prepared by reacting a cycloalkanone-2-carboxylate with an amine to form the 2-aminocarbonyl derivative, and then reacting this with hydrogen sulphide to form the 2-aminocarbonylcycloalken-1-yl thiol. Alternatively, and more preferably, the cycloalkanone-2-carboxylate is reacted with hydrogen sulphide to form a 1-mercaptocycloalken-1-yl-2-carboxylate, which is reacted with an amine to form the thiol-amide.

Thus, as a still further aspect of the present invention, there is provided a process for the preparation of a thiol-amide of general formula IIIa which comprises reacting a 1-mercaptocycloalken-1-yl-2-carboxylate of the general formula VI with an amine of the formula $HNR^5R^6$

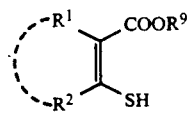

VI wherein $R^1$ and $R^2$ and $R^5$ and $R^6$ are as hereinbefore defined; and $R^9$ is a hydrocarbyl or substituted hydrocarbyl group.

The hydrocarbyl group $R^9$ preferably contains not greater than 12 carbon atoms, and typically not more than 8 carbon atoms. When $R^9$ is substituted hydrocarbyl, it is a hydrocarbyl group containing at least one hetero atom selected from nitrogen, oxygen, or sulphur and/or contains halogen such as fluorine, chlorine or bromine.

Preferably $R^9$ is alkyl containing not more than 12 carbon atoms and especially not more than 8 carbon atoms which may be linear or branched.

We have found that the reaction proceeds well when $R^9$ is $C_1-C_4$ alkyl such as methyl.

The reaction of the carboxylate with the amine may be effected under mild conditions depending on the particular amine. The amine may be one in which $R^5$ and $R^6$ are both hydrogen, i.e. ammonia, so that the final disulphide product is bis(2-aminocarbonylcycloalk-1-enyl)disulphide. If it is desired to obtain a disulphide in which the amino group is substituted at least one of the groups $R^5$ and $R^6$ should be other than hydrogen and preferably a hydrocarbyl group or substituted hydrocarbyl or $R^5$ and $R^6$ together with the nitrogen atom should form a ring. The groups $R^5$ and $R^6$ may thus be an alkyl, cycloalkyl, alkenyl, aryl, aralkyl or alkaryl group and typically contain up to 20 carbon atoms, and especially 1 to 12 carbon atoms. It is generally preferred that $R^5$ is hydrogen and $R^6$ is either hydrogen or an alkyl group.

The reaction of the carboxylate with the amine is effected in a suitable solvent which may be water if the amine is a lower alkyl amine such as methylamine. With amines in which at least one of the groups $R^5$ or $R^6$ is a higher alkyl group, it may be necessary to use other solvents, for example hydrocarbon solvents such as hexane, toluene, xylene and petroleum ether or mixtures thereof. The use of a water-immiscible solvent is generally preferred in order to ease the separation of the thiol-amide from unreacted amine.

The reaction between the carboxylate and the amine occurs readily and when using lower alkyl amines a reaction temperature which is close to ambient temperature is satisfactory. More specifically the reaction temperature generally does not exceed 50° C. and preferably is not more then 40° C., especially from 25° to 30° C.

The carboxylate is conveniently added to a solution of the amine, for example an aqueous solution. The concentration of amine may be in the range from 10% by weight up to essentially 100% by weight although such high concentrations are undesirable with lower alkyl amines which have low boiling points and hence are readily volatilised even at ambient temperature and below. The amine concentration is conveniently from 20% to 60% by weight, for example 40% by weight.

The amine is preferably used in a molar excess relative to the carboxylate. Typically at least 2 moles of amine are used for each mole of the carboxylate and up to 20 moles of amine may be used but no advantages are believed to be attained by the use of greater proportions of the amine. We have obtained satisfactory results using ten moles methylamine for each mole of the carboxylate.

The process of the reaction may be monitored by appropriate analytical techniques, for example by liquid phase chromatography. Under the conditions set out herein, we have found that the reaction is typically complete in about six hours.

The reaction product is an amide which forms a precipitate when the reaction is effected in water. The excess, unreacted, amine can be removed from the reaction mixture by distillation under reduced pressure, for example at a pressure of 50 mm of mercury or less which can be achieved using a water pump.

The solid thiol-amide can be recovered from the reaction mixture by any suitable means, such as filtration and the solid washed and dried, if desired.

The thiol-amides prepared as above may be readily purified. Thus, where the amine is ammonia or methylamine the excess amine can be removed by simply washing with water. Where the amine is less water-soluble, excess amine may be removed by washing with dilute aqueous acid. Alternatively, the thiol-amide may be dissolved in aqueous alkali and the excess amine extracted into a suitable solvent. The thiol-amide may then be recovered by neutralisation and filtration.

The thiol-amide may be used to prepare a disulphide of general formula I as hereinbefore described or it may be used to prepare a polymethylene-4-isothiazolin-3-one using a cyclisation step as described in GB 2176187.

In various types of applications, it is frequently necessary or convenient to formulate the bis(2-aminocarbonylcycloalk-1-enyl)disulphide of general formula I in a suitable liquid medium, especially water or a polar organic solvent such as an alcohol.

The disulphide compounds of the present invention have antimicrobial properties and are suitable for use as industrial biocides. They exhibit good wet state preservation and hence may be used to inhibit microbial growth in a cutting fluid preservative, cooling waters and paper mill liquors. The compounds may also be used to preserve industrially important formulations, especially aqueous based formulations, which are used for coloration, such as dyestuffs and printing inks and agrochemical formulations such as herbicide and pesticide flowables.

Still further important applications of the compounds of the present invention include their use in hydrocarbon fluids such as diesel fuels, adhesives or cosmetics in order to inhibit microbial spoilage and in the preservation of wood and leather.

The compounds of the present invention are especially useful in the preservation of paints, especially aqueous-based latices.

Preferred latices are polyvinyl acrylate and particularly acrylic latices, especially those with a pH above 7, and more especially those containing ammonia or amines.

The compositions of the present invention may be used alone or in conjunction with a suitable carrier.

Thus, as a further aspect of the present invention there is provided a biocide composition comprising a carrier and an effective amount of a compound of general formula I in accordance with the invention.

The carrier is typically a medium which shows little, if any, antimicrobial activity and may be, or include, a material which is susceptible to the growth of microorganisms, such as bacteria. The carrier is preferably a liquid medium and the biocide composition is preferably a solution, suspension or emulsion of the compound of general formula I in a liquid carrier. The carrier may be water or a hydrophilic solvent such as acetic acid, N,N-dimethylformamide, propylene glycol, ethylene diamine, dimethyl sulphoxide or N-methyl-2-pyrrolidone or a mixture of such liquids. If the composition is in the form of a suspension or emulsion, this preferably contains a surface active agent in order to inhibit phase separation. Any surface active agent known for use in biocide compositions may be used in such a system, for example alkylene oxide adducts of fatty alcohols, alkyl phenols, and anionic surfactants such as those obtained by reacting naphthol sulphonates with formaldehyde.

The amount of the compound or compounds of general formula I which is present in the biocide composition may be just sufficient to have an antimicrobial effect or may be present substantially in excess of this amount. It will be appreciated that the biocide composition may be provided as a concentrated solution for bulk transportation and subsequently diluted for use in antimicrobial protection. Thus, the amount of the compound of general formula I which is present in the biocide composition is typically in the range from 0.0001% up to 30% by weight of the biocide composition.

The composition of the present invention is especially effective in providing anti-bacterial activity. Thus, the compositions can be used for the treatment of various media to inhibit the growth of micro-organisms.

As a further aspect of the present invention there is provided a method for inhibiting the growth of micro-organisms on, or in, a medium which comprises treating the medium with a compound of the general formula I or a composition containing a compound of general formula I as hereinbefore defined.

The composition can be used in systems in which micro-organisms grow and cause problems. These systems include liquid, particularly aqueous, systems for example cooling water liquors, paper mill liquors, metal working fluids, geological drilling lubricants, Polymer emulsions and surface coating compositions such as paints, varnishes and lacquers, and solid systems such as wood and leather. The composition of the present invention can be included in such systems to provide an anti-microbial effect. The amount of the composition is typically from 0.0001 up to 10%, preferably 0.001 up to 5% and especially 0.002 to 0.1% by weight relative to the system to which it is added. In many cases, microbial inhibition has been achieved with from 0.0005% to 0.01% by weight of the composition.

The compounds of general formula I may be the only biologically active compounds of the composition of the present invention may be the only antimicrobial compounds or the composition may comprise further compounds having antimicrobial characteristics. The composition may contain more than one compound of general formula I. Alternatively, a composition of compound I in accordance with the present invention may be used together with one or more other antimicrobial compounds. The use of a mixture of anti-microbial compounds can provide a composition having a broader anti-microbial spectrum and hence one which is more generally effective than the individual components thereof. The other antimicrobial may be one possessing anti-bacterial, anti-fungal, anti-algal or other antimicrobial characteristic. The mixture of compound I of the pre sent invention with other antimicrobial compounds typically contains from 1 to 99% b weight, and particularly from 40 to 60% by weight, relative to the weight of total antimicrobially active compounds, of compound I.

Examples of known antimicrobial compounds which may be used, together with compound I are quaternary ammonium compounds such as diethyldodecylbenzyl ammonium chloride; dimethyloctadecyl-(dimethylbenzyl)ammonium chloride; dimethyldidecylammonium chloride; dimethyldidodecylammonium chloride; trimethyl-tetradecylammonium chloride; benzyldimethyl($C_{12}$–$C_{18}$ alkyl)ammonium chloride; dichlorobenzyldimethyldodecylammonium chloride; hexadecylpyridinium chloride; hexadecylpyridinium bromide; hexadecyltrimethylammonium bromide; dodecylpyridinium chloride; dodecylpyridiriium bisulphate; benzyldodecyl-bis(beta-hydroxyethyl)ammonium chloride; dodecylbenzyltrimethylammonium chloride; benzyldimethyl($C_{12}$–$C_{18}$ alkyl)ammonium chloride; dodecyldimethylethyl ammonium ethylsulphate; dodecyldimethyl-(1-napththylmethyl)ammonium chloride; hexadecyldimethylbenzyl ammonium chloride; dodecyldimethylbenzyl ammonium chloride and 1-(3-chloroallyl)-3,5,7-triaza- 1-azonia -adamantane chloride; urea derivatives such as 1,3-bis(hydroxymethyl) -5,5-dimethylhydantoin; bis(hydroxymethyl)urea; tetrakis (hydroxymethyl)acetylene diurea; 1-(hydroxymethyl)-5,5,-dimethylhydantoin and imidazolidinyl urea; amino compounds such as 1,3-bis(2-ethyl-hexyl)-5-methyl-5-aminohexahydropyrimidine; hexamethylene tetramine; 1,3-bis(4-aminophenoxy)propane; and 2-[(hydroxymethyl)-aminolethanol; imidazole derivatives such as 1[2-(2,4-dichlorophenyl)-2-(2-propenyloxy)ethyl]-1H-imidazole; 2-(methoxycarbonylamino)-benzimidazole; nitrile compounds such as 2-bromo-2-bromomethyl-glutaronitrile, 2-chloro-2-chloromethylglutaronitrile; and 2,4,5,6-tetra-chlorosisophthalodinitrile; thiocyanate derivatives such as methylene bis thiocyanate; tin compounds or complexes such as tributyltin-oxide, chloride, naphthoate, benzoate or 2-hydroxybenzoate; isothiazolin-3-ones such as 4,5-trimethylene-4-isothiazolin-3-one, 2-methyl-4,5-trimethylene-4-isothiazolin-3-one, 2-methyl isothiazolin-3-one, 5-chloro-2-methyl-isothiazolin-3-one, benzisothiazolin-3-one and 2-methyl benzisothiazolin-3-one; thiazole derivatives such as 2-(thiocyanomethylthio)-benzthiazole; and mercaptobenzthiazole; nitro compounds such as tris(hydroxymethyl)-nitromethane; 5-bromo-5-nitro-1,3-dioxane and 2-bromo-2-nitropropane-1,3-diol; iodine compounds such as iodo propynyl butyl carbamate and tri-iodo allyl alcohol; aldehydes and derivatives such as gluteraldehyde (pentanedial), p-chlorophenyl -3-iodopropargyl formaldehyde and glyoxal; amides such as chloracetamide; N,N-bis(hydroxymethyl)chloracetamide; N-hydroxymethyl-chloracetamide and dithio-2,2-bis(benzmethyl amide); guanidine derivatives such as poly hexamethylene biguanide and 1,6-hexamethylene-bis[5-(4-chlorophenyl)biguanide]; thiones such as 3,5-dimethyl-tetrahydro-1,3,5-2H-thiodiazine-2-thione; triazine derivatives such as hexahydrotriazine and 1,3,5-tri-(hydroxyethyl)-1,3,5-hexahydrotriazine; oxazolidine and derivatives thereof such as bis-oxazolidine; furan and derivatives thereof such as 2,5-dihydro-2,5-dialkoxy-2,5-dialkylfuran; carboxylic acids and the salts and esters thereof such as sorbic acid and the salts thereof and 4-hydroxybenzoic acid and the salts and esters thereof; phenol and derivatives thereof such as 5-chloro-2-(2,4-dichlorophenoxy)phenol; thio-bis(4-chlorophenol) and 2-phenylphenol; sulphone derivatives such as diiodomethyl-paratolyl sulphone, 2,3,5,6-tetrachloro-4-(methylsulphonyl) pyridine and hexachlorodimethyl sulphone.

Further aspects of the present invention are described in the following illustrative examples wherein all quantities are given as parts by weight unless stated to the contrary.

In the following examples, the compounds in accordance with the present invention were subjected to evaluation of the antimicrobial properties under sterile conditions as detailed below:

In the microbiological testing, the compounds were tested for anti-microbial activity against bacteria, fungi and a yeast. The bacteria used were one or more of *Escherichia coli, Pseudomonas aeruginosa, Staphylococcus aureus* and *Bacillus subtilis*. The fungi/yeast used were one or more of *Aspergillus niger, Candida albicans, Aureobasidium pullulans, Gliocladium roseum* and *Penicillium pinophilum*.

These test organisms will be referred to hereafter as EC, PA, SA, BS, AN, CA, AP, GR and PP respectively.

Microbiostatic Evaluation

The material to be tested was dissolved in a suitable solvent and the solution obtained diluted with a further quantity of the same solvent to give a desired product concentration.

To a suitable agar medium was added a quantity of the product solution to give a desired concentration of the product. The agar medium containing the product was poured into petri dish plates and allowed to set.

The test organisms were surface inoculated onto the test plates by means of a multi-point inoculator. Each test plate was inoculated with bacteria, fungi and yeast. The plates were incubated for four days at 25° C.

At the end of the incubation period, the plates were assessed visually for growth of the micro-organisms. The concentration of the product which inhibited the growth of a particular micro-organisms was recorded. This is the minimum inhibitory concentration (M. I. C.).

Generally, the compounds are evaluated against bacteria at the 25 and 100 ppm levels, and against fungi and yeast at the 5, 25 and 100 ppm levels.

EXAMPLE 1

Preparation of bis(2-aminocarbonylcyclopent-1-enyl)disulphide.

2-aminocarbonylcyclopentanone (28.25 parts) was added to methanol (88 parts) with stirring until the amide was almost completely dissolved. Sulphuric acid (98%, 110 parts) was then slowly added, maintaining the temperature below 35° C. by external cooling. The reaction mass was then cooled to 20°-25° C. and transferred to a vessel equipped with a hydrogen sulphide scrubbing unit.

Hydrogen sulphide (9.35 parts) was slowly bubbled through the reaction mass with agitation over approximately 5 hours, and the temperature maintained at 20°-25° C. by external cooling.

The reaction mass was stirred for a further 1.5 hours, and then drowned out into distilled water (383 parts) and crushed ice (110 parts) with rapid agitation. Methylene chloride (292 parts) was then added, agitated for 10-15 mins before stopping the stirring and allowing the methylene chloride to separate and form a lower phase. The methylene chloride layer was then separated and the aqueous phase washed twice with methylene chloride (2×292 parts).

The methylene chloride phase containing the 2-aminocarbonylcyclopent-1-enyl thiol was then warmed to reflux (40° C.) to degas any remaining hydrogen sulphide. The reaction mass was then cooled to 25° C. and sulphuryl chloride (14.63 parts) slowly added with stirring and maintaining the temperature below 30° C. by external cooling.

After addition of the sulphuryl chloride, the reactants were stirred for a further 15 minutes, then the separated disulphide was filtered off and washed with methylene chloride and dried to give 30 parts of the "disulphide dihydrochloride". This was then slurried in water, neutralised with aqueous sodium hydroxide solution, filtered, washed with water and dried to give the bis(2-aminocarbonylcyclopent-1-enyl)disulphide (23.8 parts).

In microbiostatic evaluation, the bis(2-aminocarbonylcyclopent-1-enyl)disulphide was evaluated against the three bacteria noted below at 5, 10, 25, 50 and 100 ppm according to the aforementioned protocol, and gave the following values.

| | |
|---|---|
| EC | 25 ppm |
| PA | 50 ppm |
| SA | 10 ppm |

EXAMPLE 2

Preparation of bis(2-methylaminocarbonylcyclopent-1-enyl) disulphide. 2-methyl-4,5-trimethylene-4-isothiazolin-3-one (1 part) was stirred in distilled water (25 parts) at 20°-25° C. Sodium hydrosulphite (2×0.2 parts) was added in two portions over 30 minutes. Analysis by HPLC indicated the formation of two products.

The white solid which formed initially was filtered off, and recrystallised from ethanol/water to give the disulphide (0.43 parts) melting at 147°-151° C.

Elemental analysis gave the following results:

| | | | | |
|---|---|---|---|---|
| | 52.3% C | 6.7% H | 8.4% N | 19.3% S |
| $C_{14}H_{20}N_2O_2S_2 \cdot 0.5H_2O$ requires | 52.3% C | 6.5% H | 8.7% N | 19.9% S |

Proton NMR analysis in deuterated chloroform gave the following results:

Proton NMR (CDCl$_3$): 2.0(2H, —CH$_2$—CH$_2$—CH$_2$—); 2.68 (2H, —C—CH$_2$—C—C—); 2.90 (2H, —C—CH$_2$—C—S—); 2.90 (3H, —N—CH$_3$); 5.6 (1H, —NH—)

Microbiostatic evaluation gave the following MIC values:

| | | | |
|---|---|---|---|
| EC | 25 ppm | AN | GT 100 ppm |
| PA | 100 ppm | CA | 100 ppm |
| SA | 25 ppm | AP | 100 ppm |
| BS | 25 ppm | GR | 25 ppm |
| | | PP | 100 ppm |

GT = greater than.

EXAMPLE 3

A mixed inoculum was prepared by culturing the following organisms for 24 hrs at 30° C. on nutrient agar.

| | |
|---|---|
| *Aeromonas hydrophila* | (P.R.A. 8) |
| *Proteus rettgeri* | (NCIB 10842) |
| *Pseudomonas aeruginosa* | (BSI ex P.R.A.) |
| *Serratia marcescens* | (NCIB 9523) |
| *Alcaligenes sp.* | (Lab. isolate AC4) |
| *Pseudomonas cepacea* | (Lab. isolate AC5) |
| *Pseudomonas putida* | (Lab. isolate AC7) |

Suspensions of each organism were prepared at a concentration of approximately $1 \times 10^8$ cells/ml (Thoma counting chamber) in quarter-strength by volume of Ringers solution. A mixed inoculum was prepared by combining equal volumes of each bacterial suspension.

Bis-(2-methylaminocarbonylcyclopent-1-enyl) disulphide, prepared as described in Example 1, was incorporated in 50 gm aliquots of a standard acrylic emulsion paint containing 0.2% by weight of yeast extract at the concentrations by weight indicated in the following table. These samples were inoculated on 3 separate occasions, at weekly intervals, with 1 part by volume of the mixed inoculum, and incubated at 30° C.

After contact times of 1, 3 and 7 days, a small aliquot from each sample was streaked across the surface of a nutrient agar plate and incubated at 30° C. for 2 days. The presence or absence of bacterial growth was determined visually.

The results are displayed in table 1 below, including a control containing no disulphide as bactericide.

TABLE 1

| | | Bacterial growth (a) | | | | | | | |
|---|---|---|---|---|---|---|---|---|---|
| | Concn | Week 1 Time (days) | | | Week 2 Time (days) | | | Week 3 Time (days) | | |
| Sample | (ppm) | 1 | 3 | 7 | 1 | 3 | 7 | 1 | 3 | 7 |
| Example 1 | 100 | 0 | 0 | 0 | 0 | 0 | 0 | 0 | 0 | 0 |
| | 50 | 1 | 0 | 0 | 0 | 0 | 0 | 1 | 0 | 0 |
| | 25 | 3 | 0 | 0 | 0 | 0 | 0 | 2 | 0 | 0 |
| | 12.5 | 4 | 3 | 0 | 3 | 2 | 0 | 3 | 4 | 4 |
| | 5.0 | 4 | 3 | 0 | 4 | 4 | 4 | 4 | 4 | 4 |
| | 2.5 | 4 | 3 | 3 | 4 | 4 | 4 | 4 | 4 | 4 |
| Control | 0 | 4 | 4 | 4 | 4 | 4 | 4 | 4 | 4 | 4 |

Notes to Table 1
a) 0 means no growth (no visible colonies)
1 means a trace of growth visible
2 means a light growth (a few colonies visible)
3 means moderate growth (discrete colonies visible, possibly with some coalescence)
4 means dense/confluent growth (coalescing colonies visible throughout).

EXAMPLE 4

Preparation of 4,5-trimethylene-4-isothiazolin-3-one, and 2-methyl-4,5-trimethylene-4-isothiazolin-3-one.

Bis(2-aminocarbonylcyclopent-1-enyl)disulphide dihydrochloride (16.1 parts) prepared as described in Example 1 was dissolved in a mixture of formic acid (107 parts) and methylene chloride (107 parts) by stirring at 25°–30° C.

Sulphuryl chloride (6.68 parts) was then run in rapidly with stirring and external cooling to maintain the temperature below 40° C. The reactants were then cooled to 25°–30° C. and stirred for a further 30 minutes.

The methylene chloride was then removed by vacuum distillation (Torr) at below 35° C. The vacuum was then further reduced (20–25 Torr) to remove some of the formic acid (boiling at 30° C. at 52 mm Hg pressure, and 40° C. at 82 mm Hg pressure). Distillation was continued until approximately 7.2 parts formic acid has been removed.

The reaction mass was then drowned out into distilled water (200 parts) with rapid stirring. At this stage the 4,5-trimethylene-4-isothiazolin-3-one could be recovered by neutralisation and extraction into methylene chloride. In this case, however, it was converted in situ to the N-methyl analogue without isolation.

Aqueous sodium hydroxide solution (146 parts, 31% by weight) was slowly added with stirring to the drown out liquors to neutralise the remaining formic acid and the hydrochloric acid from the disulphide dihydrochloride starting material. The temperature was maintained below 30° C. by external cooling. Further caustic liquor was added to adjust the pH of the liquor to approximately 9, and dimethyl sulphate (10.8 parts) was slowly added with stirring over 1 to 1½ hours, whilst maintaining the pH at 9.0±1.0 by addition of further caustic soda solution, and keeping the temperature below 30° C. by external cooling.

After addition of the dimethyl sulphate, methylene chloride (100 parts) was added, and the reaction mass stirred for a further 30 minutes. Agitation was then stopped, and the methylene chloride allowed to form a lower phase before being separated. The aqueous phase was then extracted with a further addition of methylene chloride (100 parts).

The methylene chloride liquors were then combined, and the solvent removed by evaporation to give the 2-methyl-4,5-trimethylene-4-isothiazolin-3-one as a white solid (10 parts).

EXAMPLE 5

Preparation of bi(2-butylaminocarbonylcyclopent-1-enyl)disulphide.

2-butyl-4,5-trimethylene-4-isothiazolin-3-one (0.64 parts) was dissolved in distilled water (20 parts) with stirring and two portions of sodium hydrosulphite ($2 \times 0.2$ parts) were added at 20°–25° C. and 30 minutes apart.

An immediate white precipitate formed, later becoming tarry. The reaction products were stirred overnight, and then dissolved by adding methanol (20 parts) and evaporated onto a silica support.

The reaction products were then separated by "flash chromatography". The silica support in the form of a column was eluted first with petroleum ether (boiling between 40° and 60° C.) followed by a mixture of petroleum ether containing increasing amounts of methylene chloride, where the methylene chloride was added in 10% increments by volume up to 100% methylene chloride. The column was then eluted with a mixture of methylene chloride and methanol, where the methanol was added in 1% increments by volume.

Each step change in the eluant system was carried out after 100 parts by volume of eluant.

The disulphide was eluted in the fraction containing 3% by volume methanol in methylene chloride. The solvent was then evaporated to give the disulphide as a sticky solid (0.26 parts).

Elemental analysis for the disulphide gave the following results:

| | 61.9% C | 8.5% H | 5.4% N | 13.4% S |
|---|---|---|---|---|
| $C_{20}H_{32}N_2O_2S_2 \cdot 0.5H_2O$ requires | 59.2% C | 8.1% H | 6.9% N | 15.8% S |

Proton NMR is deuterated dimethylsulphoxide gave the following results:

Proton NMR (DMSO): 0.85 (3H, C$\underline{H}_3$—C—); 1.25 (2H, —C$\underline{H}_2$—CH$_3$) 1.40 (2H, —CH$_2$—$\underline{CH_2}$—CH$_2$—); 1.90 (2$\underline{H}$, ring—CH$_2$—$\underline{CH_2}$—CH$_2$—); 2.65 (4H, —$\underline{CH}_2$—C—);3.16 (2H, —$\underline{N}$—$\underline{CH_2}$—C—); 7.55 (1H, —N$\underline{H}$—).

$^{13}$C NMR in deuterated dimethylsulphoxide gave the following results:

$^{13}$C NMR (DMSO): 13.6 (C$\underline{H}_3$—); 19.5 (—$\underline{CH_2}$—CH$_2$—CH$_2$—); 21.6 (—$\underline{CH_2}$—CH$_2$—CH$_2$—); 31.2 (—N—$\underline{CH_2}$—); 33.2 (—CH$_2$—$\underline{CH_2}$—CH$_2$—); 37.0 (—CH$_2$—$\underline{CH_2}$—C—C—); 38.2 (—CH$_2$—$\underline{CH_2}$—C—S—); 133.6 (—CH$_2$—$\underline{C}$—C—); 150.0 (—CH$_2$—C—S—); 164.5 ($\underline{C}$=O)

Microbiostatic evaluation for the disulphide gave the following MIC values.

| EC | 100 ppm | AN | GT 100 ppm |
|----|---------|----|-----------|
| PA | GT 100 ppm | CA | GT 100 ppm |
| SA | 25 ppm | AR | GT 100 ppm |
| BS | 25 ppm | GR | GT 100 ppm |
|    |         | PP | GT 100 ppm |

GT = greater than.

EXAMPLE 6

Preparation of bis(2-hexylaminocarbonylcyclopent-1-enyl)disulphide.

The process of Example 5 was repeated except that 2-hexyl-4,5trimethylene-4-isothiazolin-3-one (1.55 parts) was used in place of the 2-butyl isothiazolin-3-one.

The reaction products were again separated by "flash chromatography" to give the disulphide as a sticky solid (0.4 parts).

Elemental analysis for the disulphide gave the following results:

|                       | %C    | %H    | %N    | %S    |
|-----------------------|-------|-------|-------|-------|
|                       | 63.6% C | 8.8% H | 5.1% N | 12.4% S |
| C$_{24}$H$_{40}$N$_2$O$_2$S$_2$ requires | 63.7% C | 8.8% H | 6.2% N | 14.1% S |

The disulphide gave the following NMR spectrum as a solution in deuterated dimethylsulphoxide.

Proton NMR (DMSO): 0.8 (3H, C$\underline{H}_3$—C—); 1.2 (8H, multiplet —(C$\underline{H}_2$)$_4$—CH$_3$); 1.4 (2$\underline{H}$, —N—CH$_2$—C$\underline{H}_2$—C); 1.9 (2$\underline{H}$, —CH$_2$—$\underline{CH_2}$—CH$_2$—); 2.6 (4H, —$\underline{CH}_2$—CH$_2$—CH$_2$—); 3.1 (2$\underline{H}$, —N—$\underline{CH_2}$—C—); 7.6 (1$\underline{H}$, —N$\underline{H}$—)

Microbiostatic evaluation gave the following MIC values:

| EC | GT 100 ppm | AN | 100 ppm |
|----|------------|----|---------|
| PA | GT 100 ppm | CA | 100 ppm |
| SA | 25 ppm | AP | 25 ppm |
| BS | 25 ppm | GR | 100 ppm |
|    |            | PP | 25 ppm |

GT = greater than.

EXAMPLE 7

Preparation of bis(2-octylaminocarbonylcyclopent-1-enyl)disulphide.

2-octyl-4,5-trimethylene-4-isothiazolin-3-one (1.0 part) was stirred overnight at 20°-25° C. in distilled water (25 parts) and sodium hydrosulphite (0.2 part). Analysis by high performance liquid chromatography (HPLC) showed the presence of about 33% starting material. A further portion of sodium hydrosulphite (0.2 part) was added, and the reactants stirred at 20°-25° C. for a further 1 hour. Analysis by HPLC showed the reaction to be still incomplete, hence a further aliquot of hydrosulphite (0.2 parts) was added and the reactants stirred for a further 2 hours. The reaction then appeared complete by HPLC.

The disulphide which had separated was filtered off, washed with water and dried to give a white solid (0.42 parts) melting at 116°-118° C.

Elemental analysis for the disulphide gave the following results:

|                       | %C    | %H    | %N    | %S    |
|-----------------------|-------|-------|-------|-------|
|                       | 65.3% C | 9.5% H | 5.2% N | 12.5% S |
| C$_{28}$H$_{48}$N$_2$O$_2$S$_2$.0.5H$_2$O requires | 65.0% C | 9.5% H | 5.4% N | 12.4% S |

Proton NMR as a solution in deuterated chloroform gave:

Proton NMR (CDCl$_3$): 0.9 (3H, C$\underline{H}_3$—C—); 1.3 (10H, multiplet —C—(C$\underline{H}_2$)$_5$—CH$_3$); 1.5 (2H, —NC-H$_2$—CH$_2$—C—); 2.0 (2$\underline{H}$, —CH$_2$—$\underline{CH_2}$—CH$_2$—); 2.7 (2H, —$\underline{CH_2}$—CH$_2$—C—C); 2.9 (2$\underline{H}$, —CH$_2$—C$\underline{H}_2$—C—S—); 3.3 (2H, —N—C$\underline{H}_2$—C—); 5.5 (1$\underline{H}$, N$\underline{H}$—).

Microbiostatic evaluation gave the following MIC values:

| EC | GT 100 ppm | AN | GT 100 ppm |
|----|------------|----|------------|
| PA | GT 100 ppm | CA | GT 100 ppm |
| SA | 25 ppm | AP | 25 ppm |
| BS | 25 ppm | GR | GT 100 ppm |
|    |            | PP | GT 100 ppm |

GT = Greater than.

We claim:

1. A process for making a 4,5-polymethylene-4-isothiazolin-3-one by reacting a compound of general formula I

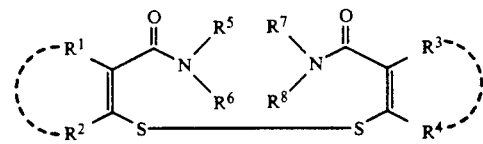

with a, oxidising agent in a solvent, wherein

R$^1$ and R$^2$ taken together, and R$^3$ and R$^4$ taken together, independently represent a polymethylene chain having 3 or 4 carbon atoms;

R$^5$ and R$^7$ are both hydrogen; and

R$^6$ and R$^8$ are independently hydrogen, hydrocarbyl or substituted hydrocarbyl.

2. A process for making a compound of general formula IV

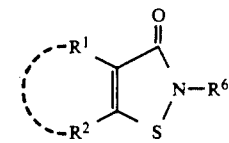

by reacting a compound of general formula v

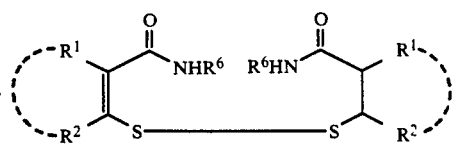

with an oxidising agent in a solvent wherein
$R^1$ and $R^2$ taken together represent a polymethylene chain having 3 or 4 carbon atoms; and
$R^6$ is hydrogen, hydrocarbyl or substituted hydrocarbyl.

3. A process as claimed in claim 1 wherein the oxidising agent is an oxyhalide of sulphur.

4. A process as claimed in claim 1 wherein the oxidising agent is sulphuryl chloride.

5. A process as claimed in claim 1 wherein the solvent is a mixture of a strong organic acid and a halogenated aliphatic hydrocarbon.

6. A process as claimed in claim 5 wherein the strong organic acid is formic acid.

7. A process as claimed in claim 5 wherein the halogenated aliphatic hydrocarbon is methylene chloride.

8. A process for making a compound of general formula V

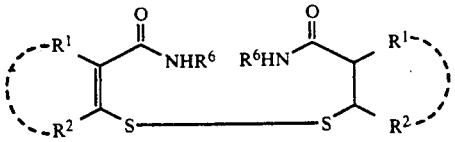

by reacting a compound of general formula IV

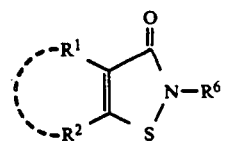

with a reducing agent in a solvent wherein
$R^1$ and $R^2$ taken together represent a polymethylene chain having 3 or 4 carbon atoms or a Polymethylene chain having 3 or 4 carbon atoms substituted by at least one lower alkyl radical having from 1 to 4 carbon atoms; and
$R^6$ is hydrogen, hydrocarbyl or substituted hydrocarbyl.

* * * * *